United States Patent [19]

Tanno et al.

[11] Patent Number: 5,225,334
[45] Date of Patent: Jul. 6, 1993

[54] METHOD AND APPARATUS FOR MEASURING CONCENTRATION OF SOLUTION OR SUSPENSION USING ELECTRICALLY HEATING METHOD

[75] Inventors: Katsutoshi Tanno, Sakato; Yasuhiko Shiinoki, Tokyo; Tomoshige Hori, Kitamoto; Kensuke Itoh, Kodaira; Tetsuo Nakamura, Iruma, all of Japan

[73] Assignee: Snow Brand Milk Products Co., Ltd., Hokkaido, Japan

[21] Appl. No.: 797,166

[22] Filed: Nov. 26, 1991

Related U.S. Application Data

[63] Continuation of Ser. No. 569,298, Aug. 20, 1990, abandoned.

[30] Foreign Application Priority Data

Aug. 30, 1989 [JP] Japan .................. 1-224235

[51] Int. Cl.$^5$ ............ G01N 25/42; C12Q 1/06; C12Q 1/04
[52] U.S. Cl. ........................... 435/39; 435/4; 435/34; 435/291; 374/45; 73/61.76
[58] Field of Search ............ 73/61 R, 61.3, 61.2, 73/61.1 R, 19.1, 61.76; 364/556, 558, 413.01; 435/4, 291, 39, 34; 374/45, 54; 422/82.12, 82.01

[56] References Cited

U.S. PATENT DOCUMENTS

| | | | |
|---|---|---|---|
| 2,779,189 | 1/1957 | Corneil | 73/61 R |
| 3,247,708 | 4/1966 | Luther | 73/61.3 X |
| 3,390,571 | 7/1968 | Roach et al. | 374/54 X |
| 3,439,528 | 4/1969 | Munitz | 73/61 R |
| 3,726,126 | 4/1973 | De Vittorio | 374/45 X |
| 3,878,049 | 4/1975 | Tannenbaum et al. | 435/4 |
| 3,963,355 | 6/1976 | Aldridge et al. | 435/39 |
| 4,009,078 | 2/1977 | Wilkins et al. | 435/39 |
| 4,197,369 | 4/1980 | Weaver | 435/4 |
| 4,226,114 | 10/1980 | Hagedorn | 73/61 R |
| 4,295,368 | 10/1981 | Jannone | 73/61.3 X |
| 4,636,089 | 1/1987 | Schumann | 374/45 |
| 4,956,793 | 9/1990 | Bonne et al. | 374/45 |
| 5,158,662 | 10/1992 | Osborne | 435/4 |

Primary Examiner—Stuart S. Levy
Assistant Examiner—Joseph A. Rhoa
Attorney, Agent, or Firm—Griffin Butler Whisenhunt & Kurtossy

[57] ABSTRACT

There is provided a circulating line branched from a solution or suspension tank and returning again to this tank through a pump (15) used to control the flow velocity at a constant level. A fluid temperature is measured by a sensor (16) in said tank or said circulating line (14) while a temperature of a heating sensor (17) employing so-called electrically heating method and placed in said circulating line is measured. Concentration of a given subject in solution or suspension is determined based on a temperature of the heating sensor or a difference between a temperature of the heating sensor and a temperature of the fluid.

4 Claims, 3 Drawing Sheets

METHOD AND APPARATUS FOR MEASURING CONCENTRATION OF SOLUTION OR SUSPENSION USING ELECTRICALLY HEATING METHOD

This application is a continuation of Ser. No. 07/569,298, filed Aug. 20, 1990, now abandoned.

BACKGROUND OF THE INVENTION

The present invention relates to method and apparatus for measuring concentration of a subject, particularly applicable to concentration measurement for microorganism or product thereof in food chemistry.

During the process of cultivating various microorganisms conventionally utilized for mass cultivation of microorganisms, collection of their products and the other purposes, it is well known to determine concentrations of such microorganisms or their products and thereby to achieve proper control of their alimentation and allowable concentrations in respective culture fluids.

Conventionally, the microorganism concentration in a culture fluid has been determined according to a basic procedure in which a portion of the culture fluid is sampled and this sample is subjected to various methods of measuring the concentration, for example, the method based on dry weight of microorganism, the nephelomatic method and the method based on microorganism population counts.

However, such basic procedure necessarily requires much time and labor, on one hand, and is practically unsuitable for the in-line measurement from the viewpoint of undesirable contamination, on the other hand.

Accordingly, there has been a serious demand for method and apparatus allowing a germless in-line measurement to be continuously performed on real time for improving efficiency of cultivation.

As the methods prior art allowing the instrumental measurement of in-line manner, (A) optical method of measurement, (B) reactive method of measurement and (C) electrochemical method of measurement have already been disclosed.

(A) Optical method of measurement using an optical apparatus comprising a sensor containing therein a light emitter and a light receptor:

Japanese Utility Model Laid-Open Application No. 1987-16457 disclose an apparatus including a light receptor adapted to convert changes in quantity of received light to changes in quantity of electricity which are, in turn, operationally processed to determine concentrations of a subject. This apparatus is of a compact structure, no interfering with circulation of the subject fluid and useful even in environment of high temperature and pressure.

Japanese Patent Laid-Open Application No. 1976-49787 discloses an apparatus for measuring concentration of microorganism or the like in a culture fluid by determining quantity of transmitted light via optical fibre. With this apparatus any microorganism sticking to the apparatus wall may be killed utilizing UV rays and said optical fibre is housed in a container provided with an openable cover so as to protect the optical fibre against adverse effect of external light and bubbles.

(B) Reactive method of measurement:

Japanese Patent Laid-Open Application No. 1987-64934 discloses a biosensor in the form of quartz oscillator having antibody immobilized on its electrode surfaces for detection and concentration measurement of microorganisms.

Japanese Patent Laid-Open Application No. 1975-36198 discloses a temperature-sensitive apparatus including a probe coated with a microorganism or enzyme to determine concentration of a molecule as the substrate of this microorganism or enzyme.

(C) Electrochemical method of measurement:

Japanese Patent Laid-Open Application No. 1985-135754 discloses an apparatus for measuring concentration of a subject. The apparatus includes a working electrode and an opposite electrode both located in a passage of solvent and portion of this passage that surround said electrodes, respectively, are of variable diameters. Concentration of a subject is determined on the basis of changes in quantity of electricity generated between said electrodes.

Japanese Patent Laid-Open Application No. 1984-81551 discloses an arrangement comprising a pair of electrodes immersed in suspension of cells and periodical potential is applied to said electrodes so as to generate an electric current. The number of cells can be determined from a value of said electric current, in view of a fact that an electric current is generated as a living cell comes in direct contact with the electrode.

Japanese Patent Laid-Open Application No. 1986-48755 discloses a system adapted to measure an electric conductivity of given culture fluid and thereby to maintain a concentration of this culture fluid a the optimum level, utilizing a phase detector for the unbalanced output from an AC bridge including a pair of electrodes placed in the culture fluid of a reference concentration and a pair of electrodes placed in a passage of the culture fluid.

However, these arrangements of prior art as have been set forth above have unsolved problems as will be described. Although the in-line measurement is essential for the closed culture system typically such as the optical apparatus for measurement as above-mentioned in (A), it has been impossible for the prior art to prevent microorganism from sticking to the sensor. In consequence, the adverse influence upon the quantity of light becomes more significant and the measuring ability is correspondingly lowered as the amount of microorganism sticking to the light emitting and receiving surfaces increases. Additionally, particularly when the medium is initially colored or progressively colored as a cultivating time elapses, transmission of light must be adversely affected. Furthermore, external light rays such as those of illumination entering through a liquid level monitoring window also adversely affect the quantity of light emitting from the light emitter. These factors may often cause false measurements.

When the medium has a relatively high viscosity, such medium also tends to stick to the light emitting and receiving surfaces due to unique configurations of the light emitter and the light receptor, making it difficult to determine the state of the medium varying thus moment by moment. Moreover, portions of the medium and the microorganism that have higher concentrations with respect to the remainders cause increased measurement errors and therefore cannot be used for the measuring purpose.

For the reactive measuring apparatus as above-mentioned in (B), the cultivation by high temperature/high pressure processing is impossible and vibration of the apparatus must be avoided because these factors might destroy the carriers immobilized on the surface of the sensor or separate microorganism, enzyme or the like from the probe. A portion of the microorganism coupled to the antibody immobilized on the sensor is not available for production and reuse of the sensor requires not only washing operation but also the other various retreatment of the used sensor, for example, immobilization of the antibody thereon, to restore its original ability.

Said reactive measuring apparatus has its application limited to enzyme or microorganism of the type that requires reaction of a reactant or catalytic action provided by such reaction and said enzyme or microorganism, if it is of a high concentration, will restrict said catalytic action. Thus, a measurable range is correspondingly limited.

Finally, the electrochemical apparatus for measurement as above-mentioned in (C) has several disadvantages. Enzyme, microorganism or the like sticking to the electrodes may cause electric troubles which may cause, in turn, a false measurement. When it is desired to wash the electrodes, types of washing that can be safely used are limited from the viewpoint of undesirable results such as corrosion. In addition, the electrodes must be detached from the apparatus before they are washed, in order to wash them reliably and satisfactorily. While proper washing is essential for the electrochemical apparatus for measurement in order to maintain the apparatus in a germless condition, such proper washing requires troublesome operation and, therefore, the electrochemical apparatus is unsuitable for a system adapted for cultivation for a long period.

The respective prior arts (A), (B), (C) have the above-mentioned problems to be solved and one of the problems common to these prior arts is the problem of bubbles inevitably generated from the medium. The bubbles, if they stick to the sensor, will lower the detecting ability of the sensor and thereby make a reliable measurement difficult. Particularly in the apparatus including the electrodes, these bubbles sticking to the electrodes may often cause an electrolytic corrosion.

SUMMARY OF THE INVENTION

It is an object of the invention to provide a method for measuring concentration of microorganism or the like adapted to avoid the technical problems encountered by said optical method of measurement, reactive method of measurement and electrochemical method of measurement, particularly the problem of bubbles generated from the medium and readily sticking to the sensor, and thereby to achieve a stabilized measurement of concentration.

The object set forth above is achieved, in accordance with the invention, by a method for measuring concentration of a given subject comprising steps of placing a heating sensor employing so-called electrically heating method in a solution or suspension, measuring a temperature of said sensor in its energized state or a differential temperature between said heating sensor in its energized state and the solution or suspension, and calculating a concentration of said given subject from said temperature of the sensor in its energized state or said differential temperature between the heating sensor in its energized state and the solution or suspension.

As for the above-mentioned method, the heating sensor is preferably current-controlled so that said heating sensor is supplied with a constant current or caused to develop a constant heat value.

To avoid a trouble for measurement due to a turbulent flow or the like occurring in a cultivating tank and thereby to achieve a stabilized concentration measurement free from various adverse effects, there is preferably provided a solution or suspension circulating line in which the heating sensor is placed.

The solution or suspension is circulated preferably at a constant velocity selected from 0.01 to 1.0 m/s and a relatively wide range of concentrations can be measured at such constant flow velocity unless it is demanded to compensate a measured value of concentration based on an actual flow velocity in order to improve its accuracy. However, it is also possible to adjust the velocity of flow variably in multistage so that a low velocity of flow is set when a high accuracy is demanded and a high velocity of flow is set when it is desired to reduce a noise.

The method of the invention as has been mentioned above is achieved by an apparatus for measuring concentration of a given subject in solution or suspension, said apparatus comprising a solution or suspension circulating line branched from a solution or suspension tank and returning again to this tank through a pump used to control the circulation at a constant velocity of flow, a sensor placed in said tank or said circulating line to determine a temperature of the solution or suspension and a heating sensor placed in said circulating line, wherein a concentration of said given subject in said solution or suspension is obtained by determining the temperature of said solution or suspension and the temperature of said heating sensor in its energized state.

In response to the sensor sensitivity and the noise level changing as the concentration of the subject in solution or suspension changes, preferably the velocity of flow is controlled in multistate by the pump so that a low velocity of flow is set when a high sensitivity is demanded and a high velocity of flow is set when it is desired to reduced a noise level.

A basic principle of the invention is to determine a concentration of microorganism or its product in fluid by employing so-called hot wire method adapted to determine a change in the apparent viscosity of fluid. According to Japanese Patent Laid-Open Application No. 1987-185146 titled "Method for measuring a state of fluid" proposed by members forming a part of the inventors of the present application, change in a state of the fluid during cultivation can be detected from a change in the apparent viscosity of the fluid and concentration of microorganism or its product can be also determined from a change in the apparent viscosity, in view of a fact that the apparent viscosity changes as the concentration increases.

For example, a heat transfer coefficient $\alpha$ representing an actual state of heat transfer is given by a following equation:

$$\alpha = Q/S(\theta_s - \theta_\infty)$$

where
Q: heat value
S: surface area of the sensor
$\theta_s$: surface temperature of the sensor
$\theta_{2s}$: temperature of surrounding fluid As will be apparent from this equation, the differential temperature between the heating sensor and the fluid surrounding the heat sensor is in a specific relationship with the concentration of microorganism. Accordingly, if the heat value is substantially constant, the temperature of the heating sensor or the differential temperature between the heating sensor and the fluid may be continuously measured and a change occurring in such value as the time elapses may be determined. Such change may be related to a change in the concentration to determine the concentration at a given moment.

When the heating sensor is current-controlled for the temperature of the fluid significantly changes, an equation $$Q = Ri^2$$

suggests that the heat transfer coefficient would change in response only to a change in the temperature of the fluid as a resistance R changes in response to a change in the temperature of the fluid and, as a result, the heat value changes. To avoid such change in the heat value, the current i may be controlled so as to maintain the heat value at a constant level while the temperature of the heating sensor is monitored so that the concentration measurement can be performed under a constant condition.

It should be understood that said surface temperature ($\theta_s$) of the sensor can be easily calculated from the temperature of the heating sensor ($\theta_w$) by employing the invention disclosed in U.S. Pat. No. 4,832,504 of the members forming a part of the inventors of the present application.

The heat transfer coefficient thus obtained can be correlated to the concentration of the subject in solution or suspension and, therefore, a change in the concentration can be numerically determined from a corresponding change in the heat transfer coefficient.

While it is possible from the above-mentioned prior art to measure a change in the differential temperature between the surface of the sensor and the fluid surrounding this, it is no more necessary to search a correlation of a change in said differential temperature between the surface of the sensor and the fluid surrounding this with a concentration of the subject so far as there is available a correlation between a change in the temperature of the heating sensor or in said differential temperature and a concentration of the subject.

The method and the apparatus of the invention provide effects as set forth below:

a) In the illustrated embodiment of the invention, the conventional sensor employing so-called electrically heating method (as disclosed, e.g., in U.S. Pat. No. 4,762,427, U.S. Pat. No. 4,882,571 etc) which may be manually washed without any damage to the sensor proper.

b) For the sensor as mentioned above in a), finishing treatment of the sensor surface can be easily done so as to minimize a possibility that the microorganism might stick to the sensor surface. Adverse effect of bubbles generated from solution or suspension is also minimized.

c) The sensor as mentioned above in a) is relatively tough, so washing of the sensor can be achieved by washing of the circulating line and maintained in a germless condition along with said circulating line, thus allowing the apparatus to be used for a long period cultivation.

d) The apparatus can withstand also a sterilizing process at high temperature and high pressure, allowing the cultivating line to be easily maintained in a germless condition.

e) The sensor as mentioned above in a) is free from color and concentration of the solution or suspension, allowing the concentration of microorganism to be controlled for a long period. Control of the entire cultivating system is correspondingly facilitated.

f) Velocity of flow in the circulating line may be regulated in multistage to perform a reliable measurement even in a range of high concentration of the microorganism.

g) The sensor as mentioned above in a) facilitates the maintenance required.

BRIEF DESCRIPTION OF THE DRAWINGS

The above and other objects of the invention will be seen by reference to the description taken in connection with the accompanying drawings, in which.

DETAILED DESCRIPTION OF THE INVENTION

The invention will be described by way of example in reference with the accompanying drawings.

Figure 1:
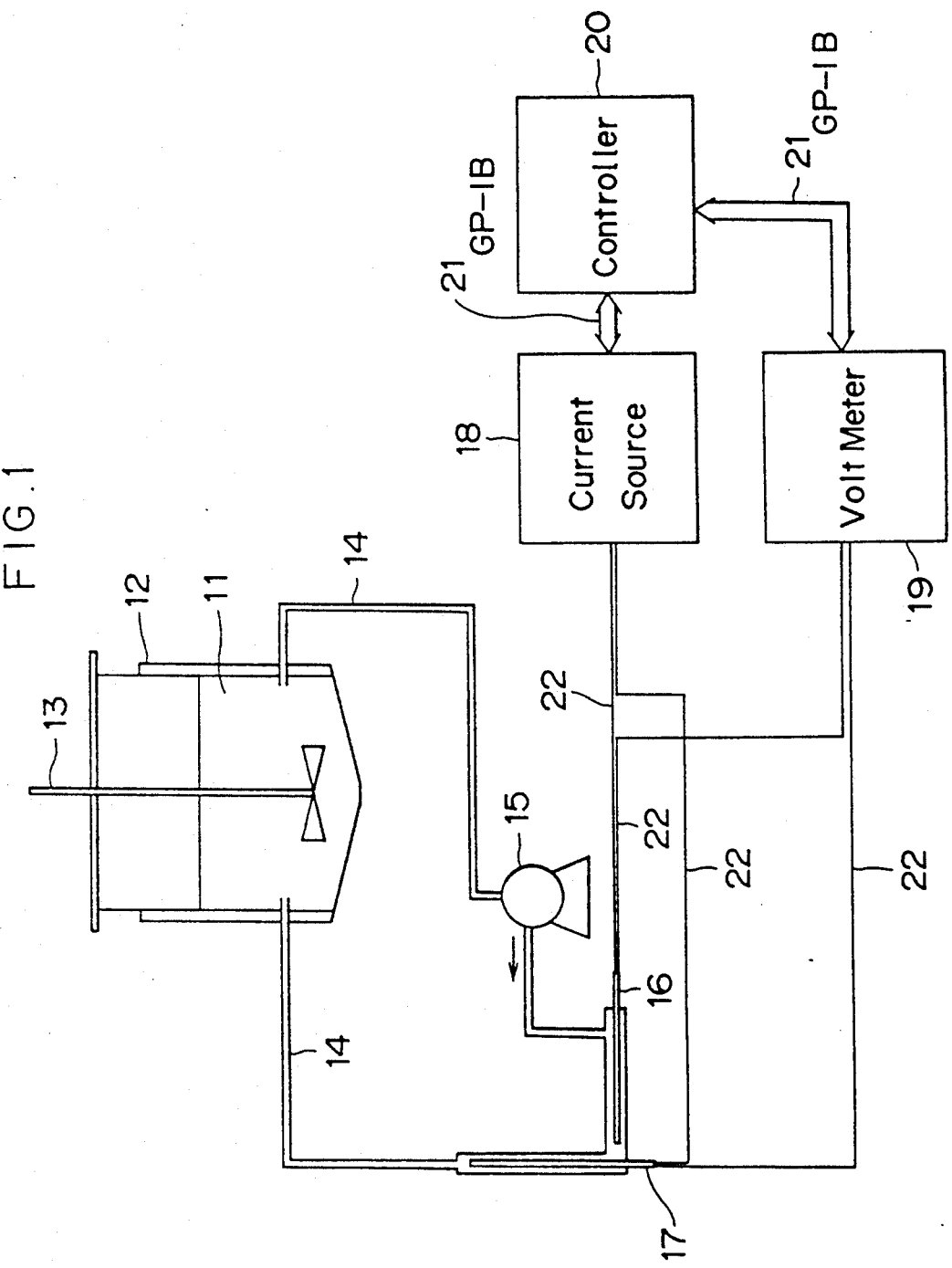
FIG. 1 schematically illustrates an embodiment of the concentration measuring apparatus constructed according to the invention.

FIG. 1 schematically illustrates an apparatus used to implement the method of the invention. Referring to FIG. 1, a container 12 equipped with an agitator 13 is filled with suspension 11 containing microorganisms or the like and then this suspension is circulated at a constant flow velocity through a circulating line 14 under action of a pump 15. A sensor 16 used to determine a temperature of the fluid and a heating sensor 17 are placed in the circulating line 14 so that a differential temperature between the heating sensor 17 and the fluid 11 can be determined.

A current source 18, a volt meter 19 and a controller 20 are interconnected by a GPIB (general purpose interface bus) 21. Reference numeral 22 designates a lead wire connecting the respective sensors 16, 17 to the current source 18 and the volt meter 19. Circulation at a constant flow velocity in the circulating line 14 is easily established by placing output of the pump 15 under control of computer or the like.

To deal with fluids of wide concentration range, it is preferably to circulate the solution or suspension at a flow velocity from 0.01 to 1.0 m/s. However, even for the fluid of which the concentration is extremely high or low, the flow velocity may be controlled in stages beyond said range to achieve a reliable measurement.

It should be noted here that said control of the flow velocity should be done in stages rather than in continuous or gradual manner, because it is desirable to maintain the flow velocity around the heating sensor at a constant value.

Orientation of the heating sensor 17 in the circulating line 14 may be vertical or horizontal and, for temperature measurement with a high accuracy, the respective sensors 16, 17 preferably comprise platinum resistors. However, they may comprise the other technical means so far as the temperature can be measured with a desired accuracy. Based on voltage V and current i applied to the respective sensors 16, 17 and resistance values R developed across the respective sensors, the temperatures $\theta_w$ of the respective sensors are calculated from an equation as follows:

$$\theta_w = (R/R_0 - 1)/R_1$$

where

R₀: resistance value of the sensor at 0° C.
R₁: temperature coefficient of the electric resistance The respective sensors 16, 17 are supplied with stabilized electric current and said sensor 16 is supplied with feeble electric current to avoid its heating.

Examples of experimental measurement conducted by using the apparatus as has been mentioned hereinabove will be described in reference with the graphic diagrams indicating the results of this measurement.

EXAMPLE 1

Figure 2:
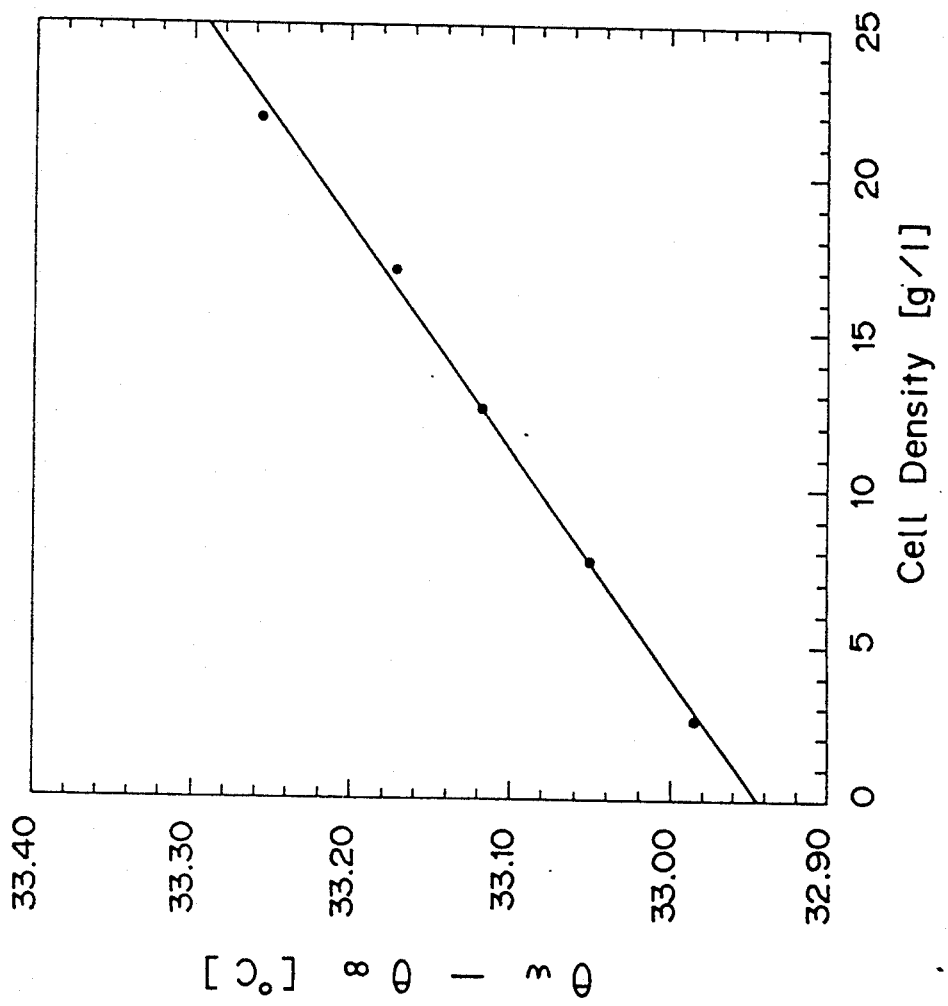
FIG. 2 is a graphic diagram illustrating the result of concentration measurement conducted on loctobacillus lactis wherein the differential temperature ($\theta_w - \theta_\infty$) between the sensor ($\theta_w$) and the fluid ($\theta_\infty$) is indicated by ordinate and the concentration of lactobacillus lactis is indicated by abscissa.

Concentration of lactic acid bacilli was measured and a result as shown in FIG. 2 was obtained. Lactic acid bacillus was dispersed in water within the container 12 until a predetermined concentration of the bacilli was reached to prepare suspension 11 which was then maintained at a temperature of 35° C. The suspension 11 was circulated through the circulating line 14 at a flow velocity of 0.3 m/s under the action of the pump 15 while the bacilli were homogeneously dispersed by rotating the agitator 13 at 250 rpm. At the same time, the heating sensor 17 was suppled with DC of 0.3 A and caused a difference $(\theta_w - \theta_\infty)$ between a sensor temperature $(\theta_w)$ corresponding to a temperature of the platinum wire contained within the heating sensor 17 and a fluid temperature $(\theta_\infty)$. A relationship between this differential temperature and the bacilli concentration is illustrated in FIG. 2. As will be apparent from FIG. 2, a specific relationship is established between the differential temperature $(\theta_w - \theta_\infty)$ and the bacilli concentration in a range of 0 to 25 g/l by dry weight. Accordingly, it is possible to determine the bacilli concentration from the differential temperature $(\theta_w - \theta_\infty)$ between the heating sensor $(\theta_w)$ and the fluid $(\theta_\infty)$.

The same result can be obtained also from the difference $(\theta_S - \theta_\infty)$ between the sensor surface temperature $(\theta_S)$ and the fluid temperature $(\theta_\infty)$. In this case, the sensor surface temperature $(\theta_S)$ is calculated, as has previously been mentioned, by employing the teachings disclosed in U.S. Pat. No. 4,832,504 of members forming a part of the inventors of the present application, then a correlation between $(\theta_S - \theta_\infty)$ and the concentration is searched, and the bacilli concentration is determined from $(\theta_S - \theta_\infty)$ based on said correlation.

EXAMPLE 2

Figure 3:
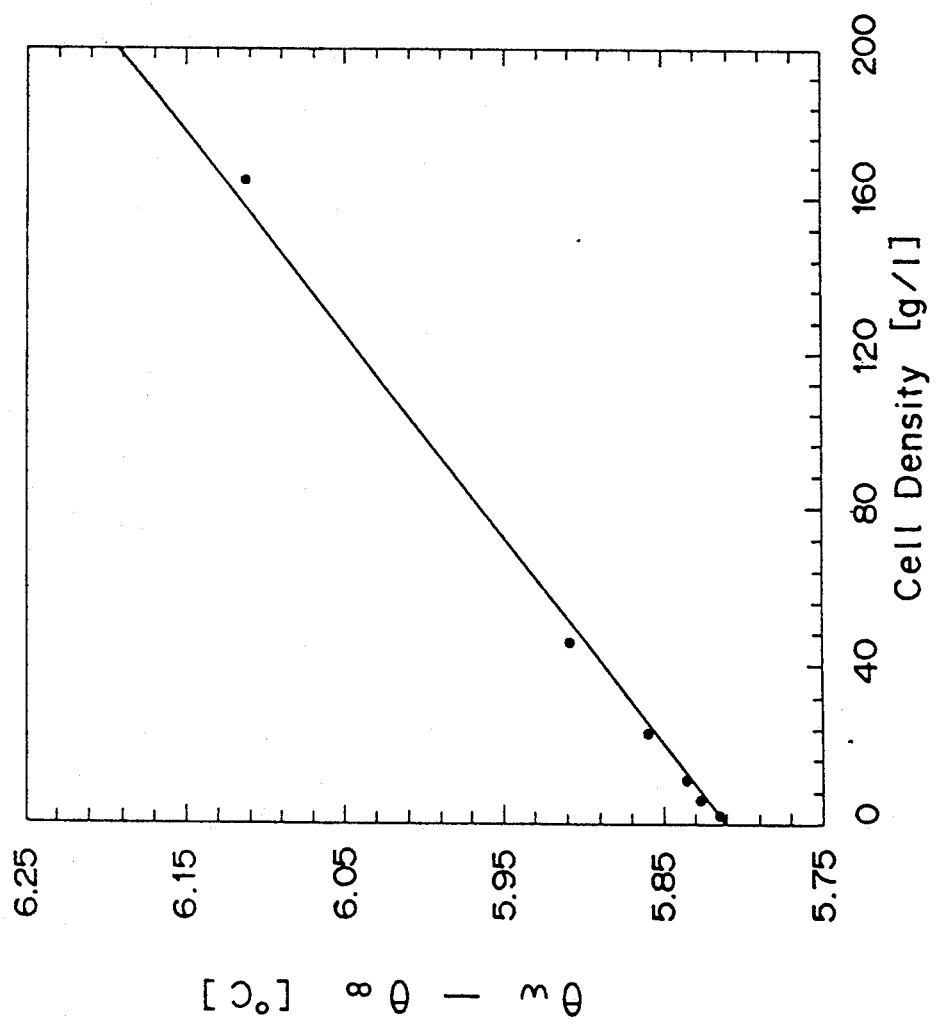
FIG. 3 is a graphic diagram illustrating the result of concentration measurement conducted on yeast fungus wherein the differential temperature ($\theta_w - \theta_\infty$) between the sensor ($\theta_w$) and the fluid ($\theta_\infty$) is indicated by ordinate and the concentration of yeast fungus is indicated by abscissa.

Concentration of yeast fungi was measured and a result as shown in FIG. 3 was obtained. Yeast fungus was dispersed in water until a predetermined concentration of the fungi was reached to prepare suspension 11 which was then maintained at a temperature of 25° C. The suspension 11 was circulated by the pump 15 at a flow velocity of 0.5 m/s. The heating sensor 17 was supplied with DC of 0.5 A, causing it to develop a desired heat, and a difference $(\theta_w - \theta_\infty)$ between a sensor temperature $(\theta_w)$ corresponding to a temperature of the platinum wire contained within the heating sensor 17 and a fluid temperature $(\theta_\infty)$. A relationship between this differential temperature and the yeast fungi concentration is illustrated in FIG. 3. As will be apparent from FIG. 3, a specific correlation is established between the yeast fungi concentration and the differential temperature $(\theta_w - \theta_\infty)$ even in a range of the concentration as high as 160 g/l by dry weight. Accordingly, it is possible to determine the fungi concentration with a high accuracy from the differential temperature $(\theta_w - \theta_\infty)$ between the heating sensor $(\theta_w)$ and the fluid $(\theta_\infty)$.

The experiment indicated that the range of 0.3 to 0.9 A is preferable as the range of current to be controlled during measurement of concentration of microorganism or its product. However, such values are not critical because such values depend on the particular design of the sensor. Though the above-mentioned examples were the case in which the concentration of the bacilli or fungi was determined based on the differential temperature, the concentration can be determined merely by measuring a temperature of the heating sensor 17 so long as a temperature of the solution of suspension is kept constant. Further another procedure of measurement is also possible, in which a heat transfer coefficient α is calculated from temperatures of the heating sensor 17 and the suspension 11, change in this heat transfer coefficient α is related to change in the concentration and thereby the concentration of the bacilli or fungi is determined from the heat transfer coefficient α based on a correlation between said α and the concentration.

With the concentration measuring method of the invention, a lower flow velocity of the solution or suspension in the circulating line certainly improves the sensitivity but tends to increase the noise and the noise is reduced but the sensitivity tends to be lowered as the flow velocity rises. Such inconvenience may be overcome by controlling the flow velocity in multistage mode so that the flow velocity is lowered when a higher sensitivity is demanded and accelerated when it is desired to reduce the noise. Such adjustment of the flow velocity permits the concentration measurement to be reliably achieved over a wide range of concentration.

This additional control allows the apparatus of the invention to be effectively used for concentration measurement in many types of solution or suspension and eliminates the complicated procedures which have been imposed on the prior art, such as selection of various instruments adapted for particular measuring purposes.

While the invention has been particularly shown and described with reference to preferred embodiment thereof, it will be understood by those skilled in the art that the foregoing and other changes in form and details can be made therein without departing from the spirit and scope of the invention.

What is claimed is:

1. A method for measuring the concentration of microorganisms in a solution or suspension thereof, comprising:
   (a) providing a tank to house the solution or suspension and a circulating line branched from the tank;
   (b) circulating the solution or suspension through the circulating line;
   (c) maintaining the solution or suspension at a substantially constant temperature throughout the circulating line;
   (d) circulating the solution or suspension through the circulating line at a substantially constant flow velocity;

(e) placing a temperature sensor in a first portion of the circulating line and measuring the temperature of the solution or suspension, using the temperature sensor;

(f) placing a heating sensor in the first portion of the circulating line and heating the heating sensor with a substantially constant energy and determining the temperature of the heating sensor;

(g) determining the temperature difference between the heating sensor and the temperature sensor; and (h) determining the concentration of the microorganisms in the solution or suspension by calculating the heat transfer coefficient from the temperature difference between the heating sensor and the temperature sensor.

2. The method as recited in claim 1, wherein the heating sensor is electrical current heated so that said heating sensor is supplied with a constant current or caused to develop a constant heat value.

3. The method as recited in claim 1, wherein a velocity of flow in the circulating line is from 0.01 to 1.0 m/s.

4. The method as recited in claim 1, wherein the velocity of flow in the circulating line is changed in multistages to measure concentration of the subject.

* * * * *